United States Patent [19]
Riendeau

[11] Patent Number: 5,474,063
[45] Date of Patent: Dec. 12, 1995

[54] TRACHEAL TUBE POSITIONING DEVICE

[76] Inventor: François J. Riendeau, 213 Bord du Lac, Pointe-Claire, Québec, Canada, H9S 4K2

[21] Appl. No.: 257,009

[22] Filed: Jun. 8, 1994

[51] Int. Cl.⁶ .................................................. A61M 16/04
[52] U.S. Cl. ........................ 128/207.18; 128/200.26; 128/911; 128/912; 128/DIG. 26; 604/94
[58] Field of Search ..................... 128/200.26, 207.14, 128/207.16, 207.18, 911, 912, DIG. 26; 604/94, 175, 301, 303; 602/74

[56] References Cited

U.S. PATENT DOCUMENTS

| | | | |
|---|---|---|---|
| D. 310,431 | 9/1990 | Bellam | D29/8 |
| D. 327,490 | 6/1992 | Wilson | D16/91 |
| 2,245,969 | 6/1941 | Francisco et al. | 128/207.18 |
| 2,259,817 | 10/1941 | Hawkins | 128/207.18 |
| 3,195,539 | 7/1965 | Hyman | 604/303 |
| 3,978,854 | 9/1976 | Mills | 128/912 |
| 4,191,180 | 3/1980 | Colley et al. | 128/DIG. 26 |
| 4,284,076 | 8/1981 | Hall | 128/207.18 |
| 4,387,471 | 6/1983 | Hsu et al. | 2/10 |
| 4,435,174 | 3/1984 | Redmond et al. | 604/174 |
| 4,465,067 | 8/1984 | Koch et al. | 128/207.18 |
| 4,480,639 | 11/1984 | Peterson et al. | 128/DIG. 26 |
| 4,574,798 | 3/1986 | Heitzman | 128/205.22 |
| 4,580,556 | 4/1986 | Kondur | 128/912 |
| 4,606,735 | 8/1986 | Wilder et al. | 604/180 |
| 4,732,147 | 3/1988 | Fuller | 128/207.18 |
| 4,774,946 | 10/1988 | Ackerman et al. | 128/207.18 |
| 4,915,104 | 4/1990 | Marcy | 128/207.18 |
| 5,042,478 | 8/1991 | Kopala et al. | 128/207.18 |
| 5,117,818 | 6/1992 | Palfy | 128/207.18 |

FOREIGN PATENT DOCUMENTS

| | | | |
|---|---|---|---|
| 2658725 | 2/1990 | France | 128/207.18 |
| 2620009 | 12/1977 | Germany | 128/DIG. 26 |

Primary Examiner—Edgar S. Burr
Assistant Examiner—William J. Deane, Jr.
Attorney, Agent, or Firm—Jacobson, Price, Holman & Stern

[57] ABSTRACT

A versatile medical device for securely positioning naso-tracheal tubes during a medical intervention such as maxillofacial surgery, wherein a comfortable naso-tracheal tube positioning device is provided, with the positioning device comprising a partial mask including a base that overlies at least a segment of the upper portion of the face of the patient, and a top portion comprising a tube holder means that securely positions the naso-tracheal tube in such a way as to permit the formation of a loop, wherein the loop is configured so as to avoid impediment or occlusion of the passage of the content thereof due to a kink in the tube while keeping the mouth area of the patient unhindered.

12 Claims, 2 Drawing Sheets

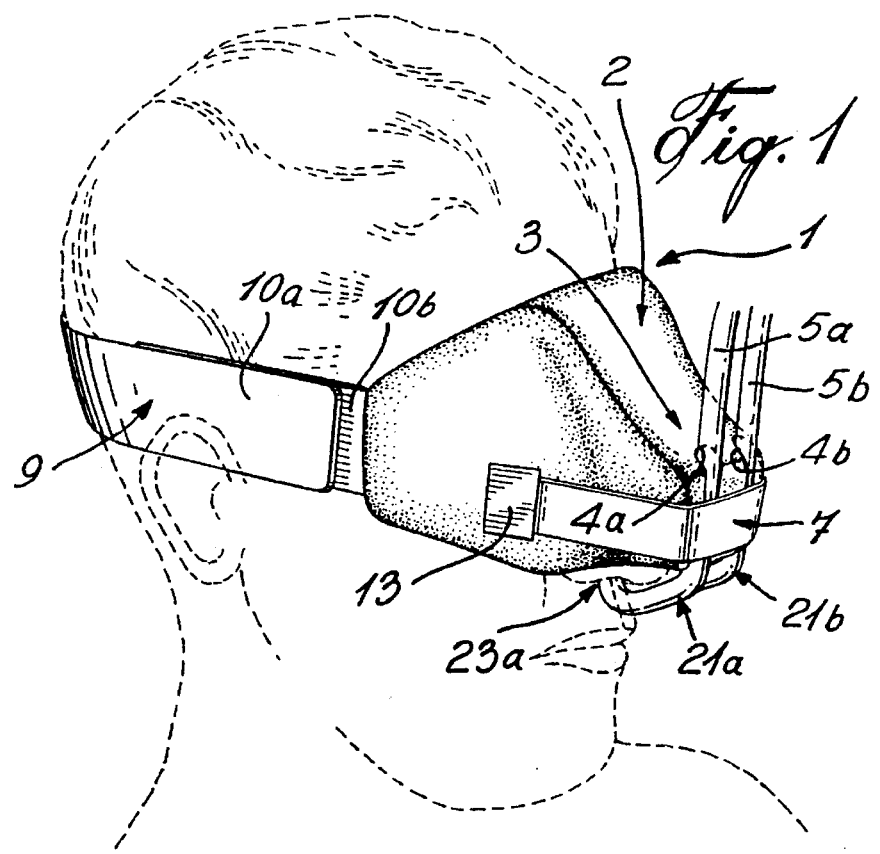
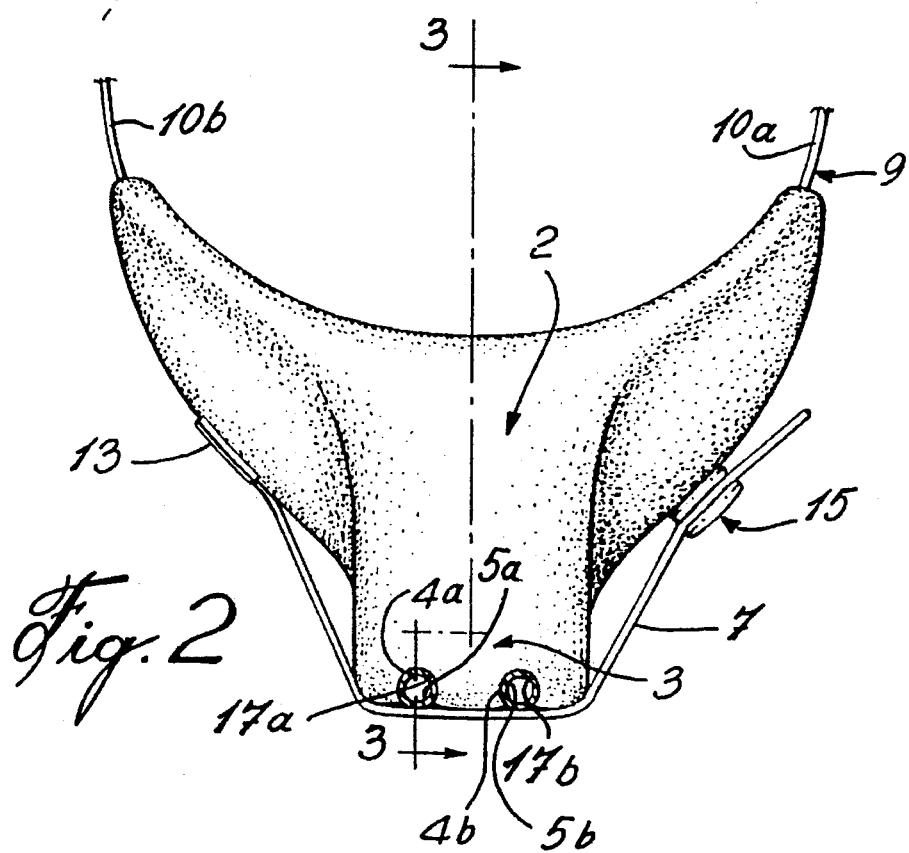

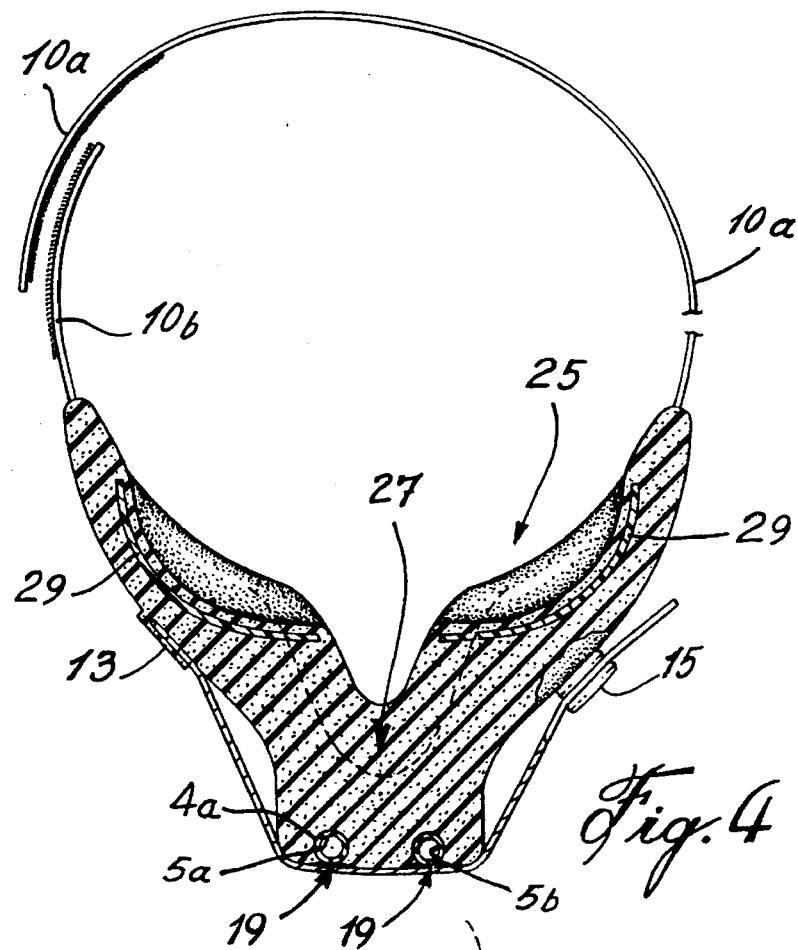
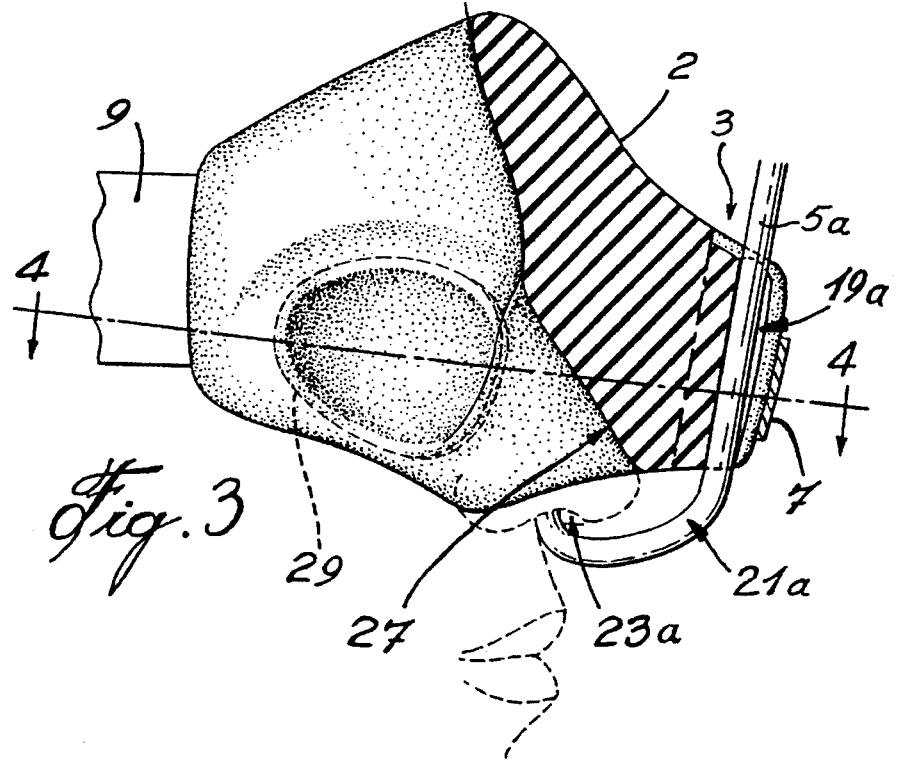

TRACHEAL TUBE POSITIONING DEVICE

BACKGROUND OF THE INVENTION

1. Field of the Invention

The present invention relates to a medical device and more particularly to a support for securing a flexible tubing inserted into the nasal passage of a patient, for preventing the disconnection of the tubing during surgery and for avoiding the formation of a kink in the flexible tubing that could obstruct the conduit therein.

2. Description of the Prior Art

A number of medical interventions require that the patient be provided with at least one tube which passes directly through his nasal conduits and into his throat, in order to provide different drugs and gases to the lungs of the patient. This nasotracheal tube must be secured such as to prevent it from falling out or from being pulled out of position.

A number of reasons warrant that utmost care be given to the secure positioning of the nasotracheal tube. For instance the naso-tracheal tube may be used by the anesthetist to provide the anesthetic to the patient. It is important that the naso-tracheal tube be securely positioned so that the content thereof be delivered to the respiratory system and not to the digestive tract as this could have life-threatening implications.

The upper portion of the face of the patient is generally covered by a sterile sheet making it difficult to assess how securely positioned the naso-tracheal tube might be at any time during the medical intervention.

Furthermore, dislodging of the nasotracheal tube can lead to injuries of the nasal conduit of the patient.

Since a number of medical interventions require that the tube or tubes be held in position for a relatively long time, it is important that the naso-tracheal tube positioning device be as stable and as comfortable as possible throughout the duration of the medical procedure.

Due to the flexible nature of the nasotracheal tube, upon bending, the tube might kink. Such a kink can obstruct or impede the flow of the contents within the tube, resulting in a release of the tube from the nasal conduit or rendering the tube ineffective in delivering the contents.

Conventionally, adhesive tape is used to secure the position of tubes, whether naso-tracheal tubes or catheters. For such tubes, the tape is placed either on the nose or the upper lip of the patient. The disadvantages of securing a tube with tape is clearly apparent. First, adhesive tape of good quality, when applied to the skin surface strongly adheres thereto and can thus cause discomfort when removed. Moreover, perspiration by the patient can contribute to the tape's inefficiency. Additionally, the region of contact between the adhesive tape and the tubing is limited, making it difficult to securely position the tube. For these and other reasons, a number of devices have been developed in an attempt to provide a relatively secure positioning of nasal tubing.

U.S. Pat. No. 2,245,969, by Francisco et al., discloses a nasal inhaler device which is similar to a pair of spectacles in that two temple portions are hooked to the patient ears while the front portion rests on the patient nose. The nasal tubes appear to be rigid or semi-rigid in this arrangement. By its design, this nasal inhaler is subject to relative instability since it is not sufficiently securely positioned. More importantly, the small surface on which the front portion of the device rests is likely to provide discomfort to the patient because of pressure sores or irritation.

The oxygen insufflation device of Koch et al., U.S. Pat. No. 4,465,067, is also a spectacle-like device, and presents the similar disadvantages.

U.S. Pat. No. 5,117,818, by Palfy, was designed to provide a more comfortable and safer means of securing nasal tubes. Palfy provides a harness with a head attachment loop and a central tube holder which rests below the nose, in the vicinity of the upper lip. The device of Palfy is a relatively complex construction with numerous adjustable parts. Its greatest disadvantage however, lies in its positioning in the close proximity to the mouth area, a fact that could be of utmost importance during a medical intervention in the area of the mouth.

The adjustable head attachment device of Hawkins, U.S. Pat. No. 2,259,817, shows a device that keeps the mouth area unhindered, thus overcoming the disadvantage of the Palfy device. However, the Hawkins head attachment device appears to be based on the use of solid or semi-solid tubing with nozzles that just superficially enter the nostrils of the patient. The Hawkins device does not appear suitable to the use of flexible tubing of the type which can pass through the nasal conduit into the patient's throat, since Hawkins does not suggest a way as to avoid a kink in flexible tubing that might impede or occlude the passage of the content thereof.

SUMMARY OF THE INVENTION

It is thus an aim of the present invention to provide a safe and comfortable means of securing at least one flexible naso-tracheal tube to a patient.

It is another aim of the present invention to provide a naso-tracheal tube positioning device that decreases anesthetic problems that can occur during surgery of the type requiring nasal intubation of the patient, due to the movement of the naso-tracheal tube. It is a further aim to avoid the movement of the naso-tracheal tube in surgeries requiring nasal intubation of the patient, such as maxillofacial surgery, plastic surgery, general surgery involving the cranial facial complex, ear-nose-and-throat surgery (ENT surgery).

It is a further aim of the present invention to provide a naso-tracheal tube positioning device which minimizes the risk of discomfort of the patient by providing a partial mask overlying at least a segment of the upper portion of the face while keeping the mouth area of the patient unhindered.

It is yet a further aim of the present invention to provide a naso-tracheal tube positioning device which is versatile in that it can fit virtually all types of faces, and in the fact that it can accommodate various types of tubes such as armed tubes or RAE™ tubes, wherein the RAE tubes can be of different sizes, 5, 6, 7, 8 or 9 mm, the choice of the size of the particular RAE tube being dependent on the internal diameter of the nasal conduit of the patient. It is contemplated that the naso-tracheal tube positioning device, of a smaller size, could be adapted to fit the facial contours of an infant or a child such as to secure naso-tracheal tubes of pediatric sizes.

An additional aim of the present invention is to provide a naso-tracheal tube positioning device that protects the eyes of the patient from potential injuries during the maxillofacial surgical treatment.

It is still a further aim of the present invention to provide a naso-tracheal tube positioning device that comprises at least one bracket which positions and secures at least one flexible tube such that it permits a proper loop to be formed between the naso-tracheal tube positioning device and the nasal passage, thereby inhibiting the formation of a kink and/or the impairment of the flow of the content of the tube.

A naso-tracheal tube positioning device in accordance with the present invention comprises a partial mask with a means to secure said mask to the head of a patient, wherein the partial mask comprises a base and a top portion, the base including a soft and skin compatible surface which overlies and corresponds to the contours of at least a segment of the upper portion of the face of the patient; the top portion comprising a tube holder means to securely position at least one naso-tracheal tube in such a way as to permit a portion of a loop to be formed between the tube holder means and the nasal passage of the patient, and wherein the loop is configured so as to avoid impediment or occlusion of the passage of the content thereof due to a kink in the tube.

The material used to make the naso-tracheal tube positioning device is optional. However, it should be understood that this material should be chosen so that the device be as safe and as comfortable as possible as well as compatible with its use as a medical device. Furthermore the material should be malleable so as to conform to the features of different types and sizes of patient's faces. Therefore, for example, light, flexible, non-allergy inducing and pleasant smelling material should be preferred.

Similarly, the device used to secure the naso-tracheal tube holder means to the head of the patient and, in a preferred embodiment, its adjustment means should provide comfort and security and be compatible with its use in medicine.

It is to be understood that the nasotracheal tube positioning device can be a reusable device or in a preferred embodiment, a disposable device.

Other features and advantages of the invention will be apparent from the description of the preferred embodiments given hereinafter. However, it should be understood that the detailed description, while indicating preferred embodiments of the invention, are given by way of illustration only, since various changes and modifications within the spirit and scope of the invention will become apparent to those skilled in the art.

BRIEF DESCRIPTION OF THE DRAWINGS

Having thus generally describe the nature of the invention, reference will now be made to the accompanying drawings, showing by way of illustration, a preferred embodiment thereof and in which:

FIG. 1 is a perspective view of the nasotracheal tube positioning device secured to the head of an individual;

FIG. 2 is a top view of the invention;

FIG. 3 is a cross-sectional view taken along section line 3—3 in FIG. 2; and

FIG. 4 is a cross-sectional view taken along line 4—4 in FIG. 3.

Referring now to the drawings and in particular to FIG. 1, there is shown a naso-tracheal tube positioning device in the form of a partial mask 1. The partial mask 1 is made of a soft, malleable and flexible material such as foam or other pliable material that can conform to the shape of the face of the patient. The partial mask has a top portion 2, the top portion 2 comprising a protruding portion 3 which includes a holder 4, 4a and 4b on the left and right sides of the partial mask, respectively. Although in general, only one naso-tracheal tube is used to intubate a patient, the partial mask in the preferred embodiments shown in the drawings, permits simultaneous intubation of both nasal passages. Furthermore, by having more than one holder, the partial mask of the preferred embodiment, facilitates the exchange from one nasal conduit to the other during the medical procedure.

The tube holder 4 secures the position of a flexible tube 5 (5a and 5b corresponding to the tubes in tube holder 4a and 4b, respectively). An optional tube securing strap 7, is also shown and is best illustrated in FIGS. 2 and 4. The partial mask 1 is secured to the head of the patient by a head positioning harness 9, which in the preferred embodiment shown in FIG. 1, comprises strap 10a and 10b, that can be tightened around the head of the patient with a fastening means such as VELCRO™.

FIG. 2 shows a more detailed view of the tube securing strap 7 anchored to the partial mask by anchor 13. The strap 7 is kept in position by fastener 15, and provides an additional device to securely position the naso-tracheal tubes on the partial mask.

As best exemplified in the embodiment shown in FIGS. 2, 3 and 4, the tube holder 4 consists of an indentation or recess 17, 17a and 17b for the left and right recess, respectively. As shown in FIG. 3, the recess 17a has a constricted neck 19a, such that the tube 5a, once inserted is held firmly in place and coaxially to the holder 4. It should be noted, that the tube holder 4 is designed so as to secure flexible tubes of different sizes such as RAE™ tubes of 5, 6, 7, 8 or 9 mm. Additionally, since the recesses 17a and 17b hold the flexible tubes 5a and 5b firmly in place, the tube securing strap 7, is optional and acts as a additional security.

As seen in FIGS. 1 and 3, the partial mask 1 and the holder 4 are designed in such a way as to permit a portion of a loop 21 to be formed between the tube holder 4 and the nasal passage of the patient 23. As best exemplified in FIG. 3, the loop is configured so as to avoid the formation of a kink in the tube and so as to keep the mouth area unhindered. It should be noted that the recesses 17a and 17b are designed such as to provide a fixed and constant location of the holder 4 relative to the nasal passages, independently of the size shape and features of the face of the patient, in order to provide the formation of a loop, thereby avoiding the formation of a kink. In addition, it is important that the holders 4 do not exert too high a pressure on the tube as to modify the flow-rate of the content thereof. The use of a soft and malleable material to make the mask 1 insures that the mask conforms to different types and sizes of faces.

As best exemplified in FIG. 4, the partial mask 1, also comprises a base 25 designed so as to conform to the facial contours of at least a segment of the upper portion of the face of a patient to distribute the pressure over a larger area of the upper portion of the face and to restrict the movement of the partial mask 1, thereby providing a stable positioning of the tube as well as comfort to the patient. The base 25 comprises a recessed portion 27 that conforms to the nose. The nose recessed portion 27 positions partial mask 1 over the nose of the patient and together with the head positioning harness 9, securely and comfortably position the partial mask over the upper portion of the patient's face.

The base 25 also comprises a pair of eye shields 29 made of a rigid material embedded in the material forming base 25. The portion of the base corresponding to the eyes of the patient, and under the shields 29, is recesses so that the base is not in contact with the eyes, adding to the comfort of the partial mask. The shields provide eye protection by distributing the pressure around the eye, so as to provide a safe and comfortable way of protecting the patient from eye injury during the medical procedure Having described the preferred embodiments of the present invention, it will appear to those ordinarily skilled in the art that various modifications may be made to the disclosed embodiments, and that such modifications are intended to be within the scope of the present invention.

We claim:

1. A tracheal tube positioning device comprising:

a partial mask adapted to be positioned above the tip of a patient's nose; the partial mask comprising a base portion, a tube positioning portion, and a head securing means for retaining the mask to the head of the patient;

the base portion including a skin compatible surface which overlies at least a substantial part of the nasal and periorbital areas of the patient's face;

the tube positioning portion comprising a tube holding means adapted to securely position at least one tracheal tube therein;

the tube holding means being spaced from the skin compatible surface such that the tracheal tube will be positioned to come down across said tube positioning portion from above and bend under said tube positioning portion adjacent the tip of a patient's nose and assume a configuration that avoids obstruction of the tube due to kinking thereof;

whereby the tracheal tube positioning device and the tube carried thereby permits access to an area of the patient's face located below the tip of the patient's nose and under medical intervention.

2. The tube positioning device of claim 1, wherein the head securing means comprises an adjustable strap and the strap is provided with a fastener.

3. The tube positioning of claim 2, wherein the tube positioning portion and base portion are in a form of a molded block of a resilient material and the holding means is a key-hole recess formed in the block such that upon insertion of the tracheal tube therein, the tracheal tube is held firmly in place and coaxially to the holding means.

4. The tube positioning device of claim 3, wherein the tracheal tube has a diameter of between 5 mm and 9 mm.

5. The tube positioning device of claim 4, further comprising a second strap connected at one end to the block and having a fastener at the other end, the second strap overlaying the recess to further hold the tube.

6. The tube positioning device of claim 2, wherein the base portion overlies the nasal and periorbital areas of the face of the patient and distributes the weight of the tube positioning device over the forehead, the temples, the bridge of the nose and around the eyes, thereby providing comfort to the patient and restricting the movement of the tube positioning device.

7. The tube positioning device of claim 2, wherein the base portion comprises concave eye shields that bridge the patient's eyes and assure distribution of the pressure around the eyes thereby protecting said eyes.

8. The tube positioning device of claim 2, wherein the positioning device is sufficiently soft and malleable to accommodate faces having different sizes and features.

9. The tube positioning device of claim 1, wherein the tube holding means is adapted to retain the tube such that an end of the tube is insertible in a suitable cavity of the patient, with the tube extending upwardly therefrom and towards the tube holding means.

10. The tube positioning device of claim 9, wherein the tube holding means is positioned substantially paralled to the patient's cerebro-spinal axis.

11. The tube positioning device of claim 1, wherein the tube holding means securely positions at least one nasotracheal tube.

12. The tube positioning device of claim 10, wherein the tube holding means securely positions at least one nasotracheal tube.

* * * * *